(12) United States Patent
Fehn

(10) Patent No.: US 7,511,110 B2
(45) Date of Patent: Mar. 31, 2009

(54) CROSSLINKABLE POLYORGANOSILOXANE COMPOSITIONS

(75) Inventor: Armin Fehn, Mehring (DE)

(73) Assignee: Wacker Chemie AG, Munich (DE)

( * ) Notice: Subject to any disclaimer, the term of this patent is extended or adjusted under 35 U.S.C. 154(b) by 410 days.

(21) Appl. No.: 11/304,191

(22) Filed: Dec. 15, 2005

(65) Prior Publication Data

US 2006/0135689 A1 Jun. 22, 2006

(30) Foreign Application Priority Data

Dec. 17, 2004 (DE) .................. 10 2004 060 934

(51) Int. Cl.
C08G 77/08 (2006.01)
(52) U.S. Cl. .................. 528/15; 528/31; 528/32; 556/9; 502/171; 502/150; 502/152; 502/155; 502/158
(58) Field of Classification Search .................. 528/15, 528/31, 32; 556/137, 9; 502/171, 150
See application file for complete search history.

(56) References Cited

U.S. PATENT DOCUMENTS

| | | | |
|---|---|---|---|
| 4,329,275 | A | 5/1982 | Hatanaka et al. |
| 4,839,452 | A * | 6/1989 | Kurita et al. .................. 528/15 |
| 5,426,200 | A | 6/1995 | Dauth et al. |
| 5,523,436 | A | 6/1996 | Dauth et al. |
| 5,561,231 | A | 10/1996 | Dauth et al. |
| 6,359,098 | B1 | 3/2002 | Fehn et al. |

FOREIGN PATENT DOCUMENTS

| | | |
|---|---|---|
| DE | 36 35 236 A1 | 5/1987 |
| EP | 0 363 006 A2 | 4/1990 |
| EP | 0 490 523 A2 | 6/1992 |
| EP | 0 545 591 A1 | 6/1993 |
| EP | 0 636 642 A1 | 2/1995 |
| EP | 0 638 604 A1 | 2/1995 |
| EP | 0 423 588 B1 | 5/1995 |
| EP | 0 491 509 B1 | 3/1996 |
| EP | 0 982 370 A1 | 3/2000 |
| EP | 0 994 159 A1 | 4/2000 |
| EP | 1 077 226 A | 2/2001 |
| EP | 1 077 226 A1 | 2/2001 |
| JP | 9-40870 | 10/1997 |

OTHER PUBLICATIONS

Butikofer, J.L., Kalberer, E.W., Schuster, W.C., Roddick, D.M., Dichloro(norbornadiene)platinum(II): a comparison with dichloro(cyclo-octadiene)platinum(II), Acta Crystallographica Section C: Crystal Structure Communications, Jun. 30, 2004, vol. C60, Part 7, pp. m353-m354. (Dichloronorbornadiene).*
English Derwent Abstract An 1987-072445 [10] Corresponding to DE 36 35 236 A1.
English Derwent Abstract An 1991-118887 [17] Corresponding to EP 0 423 588 B1.
English Derwent Abstract An 2000-206997 [19] Corresponding to EP 0 982 370 A1.
English Derwent Abstract An 2000-319924 [28] Corresponding to EP 0 994 159 A1.
English Derwent Abstract An 2001-283482 [30] Corresponding to EP 1 077 226 A1.
English Patent Abstract of Japan Corresponding to JP 09-40870.
Dinger et al., Synthesis and characterisation of platinum(II) ureylene complexes, and the X-ray structure of [Pt{PhNC(O)NAd} (COD) ] (Ad=1-adamantyl, COD=1,5-cyclo-octadiene), Journal of Organometallic Chemistry 526 (1996), pp. 303-312.
Dinger et al., "Organometallic complexes of platinum-group metals incorporating substituted guanidine dianion (triazatrimethylenemethane) ligands", Journal of Organometallic Chemistry 556 (1998) pp. 75-88.
Kemmitt et al., "Preparation and Reactivity of Platinathiadiazetidine 1,1-Dioxide and Platinadiazaphosphetidine 2-Oxide Complexes†", J. Chem. Soc. Dalton Trans. 1992, pp. 409-415.
Henderson et al., "Chemistry of Acetoacetanilide and Derivatives with Zero- and Di-valent Platinum and Palladium Complexes; Crystal Structure of the Four-membered Ring Palladalactam Complex [Pd{CH(COMe)C(O)NPh} (bipy) ] (bipy=2,2'-bipyridly)†", J. Chem. Soc. Dalton Trans. 1994, pp. 3085-3090.
Dinger et al., The first mononuclear triazatrimethylenemethane metal complex, [Pt{NPhC(NPh)NPh} (cod) ] (cod=cycloocta-1,5-diene), Chem. Commun., 1996, pp. 211-212.
Dinger et al., "Synthesis and characterisation of platinum(II) urethane complexes, and the X-ray structure of [Pt{PhNC(O)NAd} (COD)] (Ad=1-adamantyl, COD=1,5-cyclo-octadine)", Journal of Organometallic Chemistry, vol. 526, No. 2, Dec. 27, 1996, pp. 303-312.

* cited by examiner

*Primary Examiner*—Margaret G Moore
*Assistant Examiner*—Olatunde S Ojurongbe
(74) *Attorney, Agent, or Firm*—Brooks Kushman, P.C.

(57) ABSTRACT

Polyorganosiloxane compositions crosslinkable by addition of Si-bonded hydrogen to aliphatic carbon-carbon multiple bonds which have extended pot life or are preparable as storage stable one component compositions including latent catalysts of specific platinum complexes.

16 Claims, No Drawings

CROSSLINKABLE POLYORGANOSILOXANE COMPOSITIONS

BACKGROUND OF THE INVENTION

1 Field of the Invention

The present invention relates to polyorganosiloxane compositions crosslinkable by addition of Si-bonded hydrogen to aliphatic carbon-carbon multiple bonds, to processes for their preparation, to platinum catalysts used for this purpose, to the use of the crosslinkable polyorganosiloxane compositions in a process for preparing silicone elastomers, and to the use of the silicone elastomers thusly obtained.

2. Background Art

Addition-crosslinking polyorganosiloxane compositions crosslink by reaction of aliphatically unsaturated groups with Si-bonded hydrogen (hydrosilylation) in the presence of a catalyst, typically a platinum compound. Owing to the fact that the crosslinking reaction begins when simultaneous presence of the essential constituents is established, addition-crosslinking polyorganosiloxane compositions have to date been prepared virtually exclusively as two-component formulations, the composition of the individual components being such that only when they are mixed are all three essential constituents present at the same time. Typically, one of the components contains the alkenyl-functional polyorganosiloxane and the platinum catalyst, the other component the SiH-functional crosslinker, optionally in combination with further alkenyl-functional polyorganosiloxane. After the individual components have been mixed, full curing to the silicone elastomer can be effected at room temperature, but is typically carried out at elevated temperature.

Two-component systems of addition-crosslinkable polyorganosiloxane compositions are associated with numerous disadvantages, for instance, logistics, the high risk of contamination by traces of platinum, and the necessity of an additional mixing step. After the components have been mixed, a ready-to-use composition is obtained, but this composition has only a highly restricted pot life at room temperature. This restricted pot life necessitates that processing or use follow immediately, and also requires frequent cleaning of the stock vessel, metering units or processing machines, etc., since any material remaining, for example by virtue of backmixing or wall adhesion, will gel.

Owing to the disadvantages mentioned, there has been no shortage of attempts to provide addition-crosslinking polyorganosiloxane compositions as a one-component formulation (1K system). Since, in the case of a 1K system, all constituents needed for crosslinking are present together, the fundamental problem consists of suppressing premature crosslinking, which normally proceeds even at room temperature. Means of controlled adjustment, generally prolonging of the pot life of an addition-crosslinking composition, are well known, for example the use of inhibitors capable of heavily decreasing the activity of the platinum catalyst at room temperature. Examples of such inhibitors include, for example, phosphorus compounds in combination with peroxides according to U.S. Pat. No. 4,329,275 A, or azodicarbonyl compounds, as described, for example, in European Laid-Open Specification EP 0 490 523 A1. Although it is possible to prolong the pot life per se as much as desired by the type and content of such inhibitors, a disadvantageous influence of the crosslinking performance is inseparably associated with increasing pot life. This is especially true when the pot life is extended to several months by high inhibitor contents, which result in the consequence of an increased curing onset temperature with simultaneously lower crosslinking rate, to the extent of under-crosslinking in many compositions.

A further, fundamentally different approach consists in encapsulating the platinum catalyst in a finely divided material which releases the platinum only at elevated temperature. This can be done, for example, by microencapsulation of the platinum catalyst with a thermoplastic silicone resin or an organic thermoplastic, as described, for instance, in the European Laid-Open Specification EP 0 363 006 A1. Owing to the preparation of the microencapsulated catalysts, this approach is very costly and inconvenient. The resin must not dissolve in the silicone rubber, since the catalyst would otherwise escape and the pot life would be drastically lowered. Furthermore, the microencapsulated catalyst is heterogeneously distributed in the silicone, which has an adverse effect on the crosslinking, since the polyorganosiloxane composition cannot thus crosslink homogeneously. A further approach to extending pot life is the inclusion of the catalyst in a cyclodextrin, as described, for example, in European Patents EP 0 423 588 B1 and EP 0 491 509 B1. However, this approach has the great disadvantage that the inclusion compounds are insoluble in silicone and thus there is again no homogeneous distribution in the silicone. As a result, the crosslinking time is very slow even at elevated temperatures; these crosslinkable polyorganosiloxane compositions are unsuitable for processing in injection molding. A further approach employs specific platinum complexes whose activity is "latent" such that, although the hydrosilylation reaction proceeds rapidly at elevated temperature, at room temperature, the reaction rate is low enough that pot lives of several months are achieved. Polyorganosiloxane compositions which addition-crosslink with initiation by means of UV radiation and comprise platinum complexes have been described, for example, in the Japanese Laid-Open Specification JP09-040870 A2 and in the German Laid-Open Specification DE 36 35 236 A1. Further platinum complexes are disclosed in the Patents EP 0 982 370 A1, EP 0 994 159 A1 and EP 1 077 226 A1.

Even though the compositions described, especially those mentioned in the last two patents, have distinctly improved pot lives with sometimes sufficiently high crosslinking rates, there is still a need to improve the pot life and crosslinking rate of addition-crosslinking polyorganosiloxane compositions, especially those with a one-component formulation, by higher-performance platinum catalysts, without having to accept the disadvantages of the prior art mentioned above. In particular, there is a need for compositions with lower onset temperatures, but nevertheless long pot lives at room temperature.

SUMMARY OF THE INVENTION

It has now been surprisingly discovered that crosslinkable addition-curing organopolysiloxane compositions with low onset temperatures, but which also exhibit both long room temperature pot life and efficient elevated temperature crosslinking, may be prepared by employing specific cyclic platinum catalysts as described more fully below.

DETAILED DESCRIPTION OF THE PREFERRED EMBODIMENT(S)

The present invention thus provides crosslinkable polyorganosiloxane compositions comprising
(A) polyorganosiloxanes which bear radicals having aliphatic carbon-carbon multiple bonds,
(B) polyorganosiloxanes with Si-bonded hydrogen atoms, or, instead of or in conjunction with (A) and (B), (C) polyorganosiloxanes which have SiC-bonded radicals with aliphatic carbon-carbon multiple bonds and Si-bonded hydrogen atoms, and (D) at least one platinum catalyst selected from the group consisting of

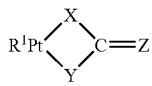 (I)

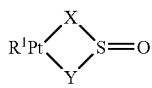 (II)

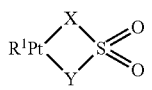 (III)

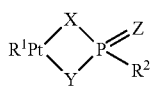 (IV)

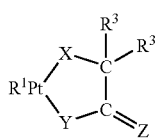 (V)

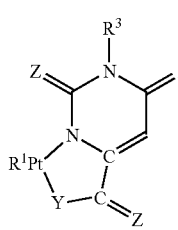 (VI)

and silanes and siloxanes comprising at least one of the unit of one of the average general formulae (VII), (VIII) or (IX)

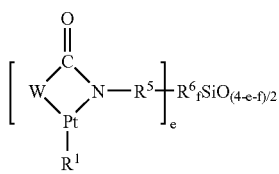 (VII)

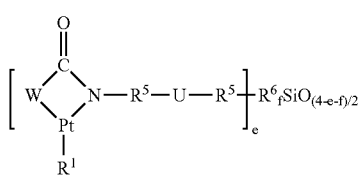 (VIII)

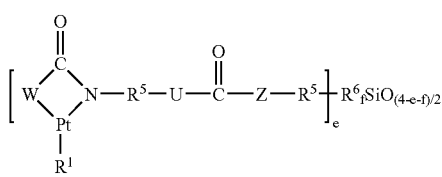 (IX)

in which $R^1$ is an optionally substituted diene which is bonded to platinum by at least one bond and is an unbranched or branched chain having from 4 to 18 carbon atoms, a cyclic or bicyclic system having from 6 to 28 carbon atoms, e is 0, 1, 2 or 3, f is 0, 1, 2 or 3, with the proviso that e+f is 4 for silanes and is 0, 1, 2 or 3 for siloxanes, and that at least one unit where e does not equal 0 is present, U is O, $NR^2$, or N—C(=O)—$NR^2$ W is $NR^7$, $C(R^3)$—$CO_2R^3$, $C(R^3)$—C(=Z)—$R^3$, S, O, or $C(R^3)_2$ X is $NR^2$, $C(R^3)$—$CO_2R^3$, $C(R^3)$—C(=Z)—$R^3$, S, O, or $C(R^3)_2$ Y is $NR^2$, $C(R^3)$—$CO_2R^3$, $C(R^3)$—C(=Z)—$R^3$, S, O, or $C(R^3)$—CN Z is O, S, Se, $NR^2$, or $CR^4_2$ $R^2$ are each independently hydrogen or a monovalent optionally substituted hydrocarbon radical having from 1 to 24 carbon atoms which optionally contains one or more heteroatoms in the chains or the rings, preferably a heteroatom selected from among the O, S, Se, N, P, and As, $R^3$ are each independently hydrogen, or a monovalent, optionally substituted hydrocarbon radical having from 1 to 28 carbon atoms, $R^4$ are each independently hydrogen, or a monovalent, optionally substituted hydrocarbon radical having from 1 to 24 carbon atoms, with the proviso that at least one radical is —CN, —$CO_2R^3$, —C(=O)—$R^3$, —$NO_2$, —C(=O)—H or halogen, $R^5$ are each independently divalent, optionally substituted hydrocarbon radicals having from 1 to 26 carbon atoms, $R^6$ are each independently monovalent, optionally substituted hydrocarbon radicals having from 1 to 20 carbon atoms and $R^7$ are each independently monovalent, optionally substituted hydrocarbon radicals having from 1 to 20 carbon atoms.

Although the compounds of the general formulae (I) to (IX) are potential inhibitors owing to the fact that they contain nitrogen and/or sulfur compounds, systems are nevertheless obtained which crosslink very rapidly at elevated temperatures, have low onset temperatures and simultaneously afford long pot lives at room temperature.

As is well known, the compounds (A) and (B) or (C) used in the inventive compositions are selected such that crosslinking is possible. For example, compound (A) may have on average at least two aliphatically unsaturated radicals and siloxane (B) may have on average at least three Si-bonded hydrogen atoms, or compound (A) may have at least three aliphatically unsaturated radicals and siloxane (B) at least two Si-bonded hydrogen atoms, or else, instead of compound (A) and (B), siloxane (C) may be used, which has aliphatically unsaturated radicals and Si-bonded hydrogen atoms in the abovementioned ratios.

The compound (A) used in accordance with the invention may also be one or more silicon-free organic compounds, preferably with at least two aliphatically unsaturated groups, and also organosilicon compounds having preferably at least two aliphatically unsaturated groups. Examples of organic compounds which can be used as component (A) in the inventive compositions are 1,3,5-trivinylcyclohexane, 2,3-dimethyl-1,3-butadiene, 7-methyl-3-methylene-1,6-octadiene, 2-methyl-1,3-butadiene, 1,5-hexadiene, 1,7-octadiene, 4,7-methylene-4,7,8,9-tetrahydroindene, methylcyclopentadiene, 5-vinyl-2-norbornene, bicyclo[2.2.1]-hepta-2,5-diene, 1,3-diisopropenylbenzene, vinyl-containing polybutadiene, 1,4-divinylcyclohexane, 1,3,5-triallylbenzene, 1,3,5-trivinylbenzene, 1,2,4-trivinylcyclohexane, 1,3,5-triisopropenylbenzene, 1,4-divinylbenzene, 3-methyl-1,5-heptadiene, 3-phenyl-1,5-hexadiene, 3-vinyl-1,5-hexadiene, and 4,5-dimethyl-4,5-diethyl-1,7-octadiene, N,N'-methylenebis(acrylamide), 1,1,1-tris(hydroxymethyl)propane triacrylate, 1,1,1-tris(hydroxymethyl)propane trimethacrylate, tripropylene glycol diacrylate, diallyl ether, diallylamine, diallyl carbonate, N,N'-diallylurea, triallylamine, tris(2-methylallyl)amine, 2,4,6-triallyloxy-1,3,5-triazine, triallyl-s-triazine-2,4,6(1H,3H,5H)-trione, diallylmalonic esters, polyethylene glycol diacrylate, polyethylene glycol dimethacrylate, and poly(propylene glycol) methacrylate.

However, the inventive silicone compositions preferably comprise, as constituent (A), an aliphatically unsaturated organosilicon compound, for which all aliphatically unsaturated organosilicon compounds useful in addition-crosslinking compositions may be used, and also, for example, silicone block copolymers with urea segments, silicone block copolymers with amide segments and/or imide segments and/or ester/amide segments and/or polystyrene segments and/or silarylene segments and/or carborane segments, and silicone graft copolymers with ether groups.

The organosilicon compounds (A) which have SiC-bonded radicals with aliphatic carbon-carbon multiple bonds, are preferably linear or branched organopolysiloxanes composed of units of the average general formula (X)

where
R may be the same or different and is an organic radical free of aliphatic carbon-carbon multiple bonds,
$R^8$ may be the same or different and is a monovalent, optionally substituted, SiC-bonded hydrocarbon radical with an aliphatic carbon-carbon multiple bond,
a is 0, 1, 2 or 3 and
b is 0, 1 or 2, with the proviso that the sum of a+b is less than or equal to 3, and, on average, at least 2 $R^8$ radicals are present per molecule.

The R radicals may be mono- or polyvalent radicals, in which case the polyvalent radicals, such as bivalent, trivalent and tetravalent radicals, may join to one another a plurality of siloxy units, for instance two, three or four siloxy units of the formula (X). R includes the monovalent radicals —F, —Cl, —Br, —$OR^9$, —CN, —SCN, —NCO and SiC-bonded, optionally substituted hydrocarbon radicals which may be interrupted by oxygen atoms or —C(O)— group(s), and also bivalent radicals Si-bonded on both sides of the formula (X).

If the R radicals are SiC-bonded, substituted hydrocarbon radicals, preferred substituents are halogen atoms, phosphorus-containing radicals, cyano radicals, —$OR^9$, —$NR^9$—, —$NR^9_2$, —$NR^9$—C(O)—$NR^9_2$, —C(O)—$NR^9_2$, —C(O)—$R^9$, —C(O)$OR^9$, —$SO_2$-Ph and —$C_6F_5$, where $R^9$ is as defined below and Ph is a phenyl radical.

Examples of R radicals are alkyl radicals such as the methyl, ethyl, n-propyl, isopropyl, n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, and octadecyl radicals such as the n-octadecyl radical, cycloalkyl radicals such as the cyclopentyl, cyclohexyl, cycloheptyl and methylcyclohexyl radicals, aryl radicals such as the phenyl, naphthyl, anthryl and phenanthryl radicals, alkaryl radicals such as the o-, m-, and p-tolyl radicals, xylyl radicals and ethylphenyl radicals, and aralkyl radicals such as the benzyl radical, and the α- and the β-phenylethyl radicals.

Examples of substituted R radicals are haloalkyl radicals such as the 3,3,3-trifluoro-n-propyl radical, the 2,2,2,2',2',2'-hexafluoroisopropyl radical, the heptafluoroisopropyl radical, haloaryl radicals such as the o-, m- and p-chlorophenyl radicals, —$(CH_2)_n$—N($R^9$)C(O)$NR^9_2$, —$(CH_2)_n$—C(O)$NR^9_2$, —$(CH_2)_n$—C(O)$R^9$, —$(CH_2)_n$—C(O)$OR^9$, —$(CH_2)_n$—C(O)$NR^9_2$, —$(CH_2)_n$—C(O)—$(CH_2)_m$—C(O)$CH_3$, —$(CH_2)_n$—$NR^9$—$(CH_2)_m$—$NR^9_2$, —$(CH_2)_n$—O—CO—$R^9$, —$(CH_2)_n$—O—$(CH_2)_m$—CH(OH)—$CH_2OH$, —$(CH_2)_n$—$(OCH_2CH_2)_m$—$OR^9$, —$(CH_2)_n$—$SO_2$-Ph and —$(CH_2)_n$—O—$C_6F_5$, where $R^9$ is as defined above, n and m are identical or different integers from 0 to 10, and Ph designates the phenyl radical.

Examples of R as bivalent radicals Si-bonded on both sides of the formula (X) are those which derive from the above monovalent examples mentioned for the R radical by substitution of a hydrogen atom for an additional bond. Examples of such radicals are —$(CH_2)_n$—, —CH($CH_3$)—, —C($CH_3$)$_2$—, —CH($CH_3$)—$CH_2$—, —$C_6H_4$—, —CH(Ph)-$CH_2$—, —C($CF_3$)$_2$—, —$(CH_2)_n$—$C_6H_4$—$(CH_2)_n$—, —$(CH_2)_n$—$C_6H_4$—$C_6H_4$—$(CH_2)_n$—, —$(CH_2O)_m$—, —$(CH_2CH_2O)_m$—, —$(CH_2)_n$—$O_x$—$C_6H_4$—$SO_2$—$C_6H_4$—$O_x$—$(CH_2)_n$—, where x is 0 or 1, m and n are each as defined above and Ph is the phenyl radical.

The R radical is preferably a monovalent, SiC-bonded, optionally substituted hydrocarbon radical which has from 1 to 18 carbon atoms and is free of aliphatic carbon-carbon multiple bonds, more preferably a monovalent SiC-bonded hydrocarbon radical which has from 1 to 6 carbon atoms and is free of aliphatic carbon-carbon multiple bonds, especially the methyl or phenyl radical.

The $R^8$ radicals may be any groups amenable to an addition reaction (hydrosilylation) with an SiH-functional compound. If the $R^8$ radicals are SiC-bonded, substituted hydrocarbon radicals, preferred substituents are halogen atoms, cyano radicals and —$OR^9$ where $R^9$ is as defined above. The $R^8$ radicals are preferably alkenyl and alkynyl groups having from 2 to 16 carbon atoms, such as vinyl, allyl, methallyl, 1-propenyl, 5-hexenyl, ethynyl, butadienyl, hexadienyl, cyclopentenyl, cyclopentadienyl, cyclohexenyl, vinylcyclohexylethyl, divinylcyclohexylethyl, norbornenyl, vinylphenyl and styryl radicals, particular preference being given to using vinyl, allyl and hexenyl radicals.

The molecular weight of constituent (A) may vary within wide limits, for instance between $10^2$ and $10^6$ g/mol. For example, constituent (A) may be a relatively low molecular weight alkenyl-functional oligosiloxane such as 1,2-divinyltetramethyldisiloxane, but may also be a highly polymerized polydimethylsiloxane having pendant or terminal Si-bonded vinyl groups, for example having a molecular weight of $10^5$ g/mol (number-average, determined by means of NMR). Nor is the structure of the molecules forming constituent (A) fixed; in particular, the structure of a relatively high molecular weight, i.e. oligomeric or polymeric, siloxane may be linear, cyclic, branched, or else resinous, network-like. Linear and cyclic polysiloxanes are preferably composed of units of the formula $R_3SiO_{1/2}$, $R^8R_2SiO_{1/2}$, $R^8RSiO_{2/2}$ and $R_2SiO_{2/2}$, where R and $R^8$ are each as defined above. Branched and network-like polysiloxanes additionally contain trifunctional and/or tetrafunctional units, preference being given to those of the formulae $RSiO_{3/2}$, $R^8SiO_{3/2}$ and $SiO_{4/2}$. It will be appreciated that it is also possible to use mixtures of different siloxanes which satisfy the criteria of constituent (A).

As component (A), particular preference is given to the use of vinyl-functional, substantially linear polydiorganosiloxanes having a viscosity of from 0.01 to 500,000 Pa·s, more preferably from 0.1 to 100,000 Pa·s, in each case measured at 25° C.

The organosilicon compound (B) used may be all hydrogen-functional organosilicon compounds which are useful in addition-crosslinkable compositions. The organopolysiloxanes (B) which have Si-bonded hydrogen atoms, are preferably linear, cyclic or branched organopolysiloxanes composed of units of the average general formula (XI)

$$R_c H_d SiO_{(4-c-d)/2} \quad (XI)$$

in which

R may be the same or different and is as defined above, c is 0, 1, 2 or 3 and d is 0, 1 or 2, with the proviso that the sum of c+d is less than or equal to 3 and, on average, at least two Si-bonded hydrogen atoms are present per molecule. The organopolysiloxane(s) (B) used in accordance with the invention preferably contain Si-bonded hydrogen in the range from 0.04 to 1.7 percent by weight based on the total weight of the organopolysiloxane (B).

The molecular weight of constituent (B) may likewise vary within wide limits, for instance between $10^2$ and $10^6$ g/mol. For example, constituent (B) may be a relatively low molecular weight SiH-functional oligosiloxane, such as tetramethyldisiloxane, but also a highly polymerized polydimethylsiloxane having pendant or terminal SiH groups, or a silicone resin having SiH groups. Nor is the structure of the molecules which form constituent (B) fixed; in particular, the structure of a relatively high molecular weight, i.e. oligomeric or polymeric, SiH-containing siloxane may be linear, cyclic, branched or else resinous, network-like. Linear and cyclic polysiloxanes are preferably composed of units of the formula $R_3SiO_{1/2}$, $HR_2SiO_{1/2}$, $HRSiO_{2/2}$ and $R_2SiO_{2/2}$, where R is as defined above. Branched and network-like polysiloxanes additionally contain trifunctional and/or tetrafunctional units, preference being given to those of the formulae $RSiO_{3/2}$, $HSiO_{3/2}$ and $SiO_{4/2}$. It will be appreciated that it is also possible to use mixtures of different siloxanes which satisfy the criteria of constituent (B). In particular, the molecules which form constituent (B), in addition to the obligatory SiH groups, may optionally at the same time also contain aliphatically unsaturated groups. Particular preference is given to the use of low molecular weight SiH-functional compounds such as tetrakis(dimethylsiloxy)silane and tetramethylcyclotetrasiloxane, and also higher molecular weight, SiH-containing siloxanes such as poly(hydromethyl)-siloxane and poly(dimethylhydromethyl)siloxane with a viscosity at 25° C. of from 10 to 10,000 mPa·s, or analogous SiH-containing compounds in which some of the methyl groups have been replaced by 3,3,3-trifluoropropyl or phenyl groups.

Constituent (B) is present in the inventive crosslinkable overall silicone compositions preferably in such an amount that the molar ratio of SiH groups to aliphatically unsaturated groups is from 0.1 to 20, more preferably between 1.0 and 5.0.

The components (A) and (B) used in accordance with the invention are commercial products or preparable by processes common in chemistry.

Instead of component (A) and (B) or in addition thereto, the inventive compositions may comprise organopolysiloxanes (C) which have aliphatic carbon-carbon multiple bonds and Si-bonded hydrogen atoms, which is, however, not preferred.

If siloxanes (C) are used, they are preferably those composed of units of the formula $$R_g SiO_{4-g/2}, R_h R^8 SiO_{3-h/2} \text{ and } R_i HSiO_{3-i/2},$$

where R and $R^8$ are each as defined above, g is 0, 1, 2 or 3, h is 0, 1 or 2 and i is 0, 1 or 2, with the proviso that at least 2 $R^8$ radicals and at least 2 Si-bonded hydrogen atoms are present per molecule.

Examples of organopolysiloxanes (C) are those composed of $SiO_{4/2}$, $R_3SiO_{1/2}$, $R_2R^8SiO_{1/2}$ and $R_2HSiO_{1/2}$ units, so-called MQ resins which may additionally contain $RSiO_{3/2}$ and $R_2SiO$ units, and also linear organopolysiloxanes substantially consisting of $R_2R^8SiO_{1/2}$, $R_2SiO$ and RHSiO units where R and $R^8$ are each as defined above.

The organopolysiloxanes (C) preferably have an average viscosity of from 0.01 to 500,000 Pa·s, more preferably from 0.1 to 100,000 Pa·s, in each case at 25° C. Organopolysiloxanes (C) are preparable by methods common in chemistry.

Examples of the $R^9$ radical are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, cycloalkyl radicals such as the cyclopropyl, cyclopentyl, cyclohexyl, cycloheptyl radicals and methylcyclohexyl radicals, unsaturated radicals such as the allyl, 5-hexenyl, 7-octenyl, cyclohexenyl and styryl radicals, aryl radicals such as phenyl radicals, o-, m- or p-tolyl radicals, xylyl radicals and ethylphenyl radicals, aralkyl radicals such as the benzyl radical and the α- and β-phenylethyl radicals, and also radicals of the formula —C(R)=CR$_2$. Examples of halogenated $R^9$ radicals are haloalkyl radicals such as the 3,3,3-trifluoro-n-propyl radical, the 2,2,2,2',2',2'-hexafluoroisopropyl radical, the heptafluoroisopropyl radical, and haloaryl radicals such as the o-, m- or p-chlorophenyl radicals.

$R^9$ is preferably a hydrogen atom, alkyl radical or aryl radical, particular preference being given to a hydrogen atom, the methyl radical and the ethyl radical.

Examples of $R^1$ are dienes, for example 1,3-butadiene, 1,4-diphenyl-1,3-butadiene, 1,3-cyclohexadiene, 1,4-cyclohexadiene, 2,4-hexadiene, 1,4-hexadiene, 1,5-hexadiene, 2,5-dimethyl-2,4-hexadiene, α- and β-terpenes, (R)-(+)-4-isopropenyl-1-methyl-1-cyclohexene, (S)-(–)-4-isopropenyl-1-methyl-1-cyclohexene, 4-vinyl-1-cyclohexene, 2,5-heptadiene, 1,5-cyclooctadiene, 1-chloro-1,5-cyclooctadiene, 1,5-dimethyl-1,5-cyclooctadiene, 1,6-dimethyl-1,5-cyclooctadiene, 1,5-dichloro-1,5-cyclooctadiene, 5,8-dihydro-1,4-dioxocine, $\eta^4$-1,3,5,7-cyclooctatetraene, $\eta^4$-1,3,5-cycloheptatriene, $\eta^4$-1-fluoro-1,3,5,7-cyclooctatetraene, $\eta^4$-1,2,4,7-tetramethyl-1,3,5,7-cyclooctatetraene, 1,8-cyclotetradecadiene, 1,9-cyclohexadecadiene, 1,13-cyclotetracosadiene, $\eta^4$-1,5,9-cyclododeca-triene, $\eta^4$-1,5,10-trimethyl-1,5,9-cyclododecatriene, $\eta^4$-1,5,9,13-cyclohexadecatetraene, bicyclo[2.2.1]hepta-2,5-diene, 1,3-dodecadiene, methylcyclopentadiene dimer, 4,7-methylene-4,7,8,9-tetrahydroindene, bicyclo[4.2.2]deca-3,9-diene-7,8-dicarboxylic anhydride, alkyl bicyclo[4.2.2]deca-3,9-diene-7,8-dicarboxylate and alkyl bicyclo[4.2.2]deca-3,7,9-triene-7,8-dicarboxylate.

The diene $R^1$ is preferably 1,5-cyclooctadiene, 1,5-dimethyl-1,5-cyclooctadiene, 1,6-dimethyl-1,5-cyclooctadiene, 1-chloro-1,5-cyclooctadiene, 1,5-dichloro-1,5-cyclooctadiene, 1,8-cyclotetradecadiene, 1,9-cyclohexadecadiene, 1,13-cyclotetra-cosadiene, bicyclo[2.2.1]hepta-2,5-diene, 4-vinyl-1-cyclohexene, and $\eta^4$-1,3,5,7-cyclooctatetraene, particular preference being given to 1,5-cyclooctadiene, bicyclo[2.2.1]hepta-2,5-diene, 1,5-dimethyl-1,5-cyclooctadiene, or 1,6-dimethyl-1,5-cyclooctadiene.

Examples of $R^2$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, norbornyl radical, octyl radicals such as the n-octyl radical, bicyclooctyl radical and isooctyl radicals such as the 2,2,4-trimethylpentyl radical, nonyl radicals such as the n-nonyl radical, decyl radicals such as the n-decyl radical and adamantyl radical, cycloalkyl radicals such as cyclopropyl, cyclopentyl, cyclohexyl, cycloheptyl radicals and methylcyclohexyl radicals, unsaturated radicals such as the allyl, 5-hexenyl, 7-octenyl, cyclohexenyl and styryl radical, aryl radicals such as phenyl radicals, o-, m- or p-tolyl radicals, xylyl radicals and ethylphenyl radicals, aralkyl radicals such as the benzyl radical and the $\alpha$- and $\beta$-phenylethyl radicals. Further examples of $R^2$ are substituted radicals such as cyano radicals, hydroxyl, methoxy, ethoxy, isopropoxy, butoxy and phenoxy radicals, and also radicals with the —$CO_2R^3$ and —$C(=O)$—$R^3$ structures.

Examples of halogenated $R^2$ radicals are haloalkyl radicals, such as the 3,3,3-trifluoro-n-propyl radical, the 2,2,2,2',2',2'-hexafluoroisopropyl radical, the heptafluoroisopropyl radical, and haloaryl radicals such as the o-, m- or p-chlorophenyl radicals.

The $R^2$ radical is preferably a hydrogen atom, a hydrocarbon radical having from 1 to 10 carbon atoms, or a radical with —$CO_2R^3$ or —$C(=O)$—$R^3$ structures, particular preference being given to the hydrogen atom, methyl radical, ethyl radical, tert-butyl radical, adamantyl radical, phenyl radical, and also radicals with the —$CO_2R^3$ and —$C(=O)$—$R^3$ structures.

Examples of $R^3$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, norbornyl radical, octyl radicals such as the n-octyl radical, bicyclooctyl radical and isooctyl radicals such as the 2,2,4-trimethylpentyl radical, nonyl radicals such as the n-nonyl radical, decyl radicals such as the n-decyl radical and adamantyl radical, cycloalkyl radicals such as cyclopropyl, cyclopentyl, cyclohexyl, cycloheptyl radicals and methylcyclohexyl radicals, unsaturated radicals such as the allyl, 5-hexenyl, 7-octenyl, cyclohexenyl and styryl radical, aryl radicals such as phenyl radicals, o-, m- or p-tolyl radicals, xylyl radicals and ethylphenyl radicals, aralkyl radicals such as the benzyl radical and the $\alpha$- and $\beta$-phenylethyl radicals; further examples of $R^3$ are substituted radicals such as cyano radicals, hydroxyl, methoxy, ethoxy, isopropoxy, butoxy and phenoxy radicals. Examples of halogenated $R^3$ radicals are haloalkyl radicals such as the trifluoromethyl radical, 3,3,3-trifluoro-n-propyl radical, the 2,2,2,2',2',2'-hexafluoroisopropyl radical, the heptafluoroisopropyl radical and haloaryl radicals such as the o-, m- or p-chlorophenyl radicals.

The $R^3$ radical is preferably a hydrogen atom or a hydrocarbon radical having from 1 to 10 carbon atoms, particular preference being given to the hydrogen atom, methyl radical, ethyl radical, tert-butyl radical and phenyl radical.

The $R^4$ radical is preferably hydrogen or a monovalent, optionally substituted hydrocarbon radicals having from 1 to 24 carbon atoms, with the proviso that at least one radical selected from the group comprising —CN, —$CO_2R^3$, —$C(=O)$—$R^3$, —$NO_2$, —$C(=O)$—H or halogen is present.

Examples of $R^4$ are hydrogen, alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical and norbornyl radical, octyl radicals such as the n-octyl radical, the bicyclooctyl radical, and isooctyl radicals such as the 2,2,4-trimethylpentyl radical, nonyl radicals such as the n-nonyl radical, decyl radicals such as the n-decyl radical, and also radicals with the —$CO_2R^3$ and —$C(=O)$—$R^3$ structures.

The $R^4$ radical is preferably a hydrogen atom, a hydrocarbon radical having from 1 to 10 carbon atoms, or a radical with a —$CO_2R^3$ and —$C(=O)$—$R^3$ structure, particular preference being given to the hydrogen atom, methyl radical, phenyl radicals and also radicals, with the —$CO_2R^3$ and —$C(=O)$—$R^3$ structures.

Examples of $R^5$ are alkylene radicals such as the methylene, ethylene, propylene, 1,6-hexylene and 2,5-hexylene radicals; arylene radicals such as the phenylene and methoxyphenylene radical; arylalkylene radicals such as —$CH_2$—$CH(CH_3)$—$C_6H_3$—$CH(CH_3)$—$CH_2$—, —$(CH_2)_n$—, —CH$(CH_3)$—, —$C(CH_3)_2$—, —$CH(CH_3)$—$CH_2$—, —$C_6H_4$—, —CH(Ph)-$CH_2$—, —$C(CF_3)_2$—, —$(CH_2)_n$—$C_6H_4$—$(CH_2)_n$—, —$C_6H_4$—$(CH_2)_n$—, —$C_6H_4$—O—$(CH_2)_n$—, —$(CH_2)_n$—$C_6H_4$—$C_6H_4$—$(CH_2)_n$—, —$(CH_2O)_m$—, —$(CH_2CH_2O)_m$—, and —$(CH_2)_n$—$O_x$—$C_6H_4$—$SO_2$—$C_6H_4$—$O_x$—$(CH_2)_n$—, where x is 0 or 1, n and m are equal or different integers from 0 to 10, and Ph denotes the phenyl radical.

The $R^5$ radical is preferably a bivalent hydrocarbon radical having from 1 to 12 carbon atoms, such as —$CH_2$—, —$C_2H_4$—, —$C_3H_6$—, —$C_4H_8$—, —$C_5H_{10}$—, —$C_6H_4$—, —$C_6H_4$—$(CH_2)_n$—, —$C_6H_4$—O—$(CH_2)_n$—.

Examples of $R^6$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical and the adamantyl radical, cycloalkyl radicals such as the cyclopropyl, cyclopentyl, cyclohexyl, cycloheptyl and methylcyclohexyl radicals, unsaturated radicals such as the vinyl, allyl, 5-hexenyl, 7-octenyl, cyclohexenyl and styryl radicals, aryl radicals such as phenyl radicals, o-, m- or p-tolyl radicals, xylyl radicals and ethylphenyl radicals, aralkyl radicals such as the benzyl radical and the $\alpha$- and $\beta$-phenylethyl radicals; further examples of $R^6$ are substituted radicals such as cyano radicals, hydroxyl, methoxy, ethoxy, isopropoxy, butoxy and phenoxy radicals, 2-methoxyphenyl, 3-methoxyphenyl, 4-methoxyphenyl, 2,4-dimethoxyphenyl, acetoxyphenyl and methoxyhydroxyphenyl radical.

Examples of halogenated $R^6$ radicals are haloalkyl radicals such as the trifluoromethyl radical, 3,3,3-trifluoro-n-propyl radical, the 2,2,2,2',2',2'-hexafluoroisopropyl radical, the heptafluoroisopropyl radical and haloaryl radicals such as the o-, m- and p-chlorophenyl radicals.

The $R^6$ radical is preferably a hydrocarbon radical having from 1 to 10 carbon atoms, particular preference being given to the methyl radical, vinyl radical, 3,3,3-trifluoro-n-propyl radical, and phenyl radical.

Examples of $R^7$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical and norbornyl radical, octyl radicals such as the n-octyl radical, the bicyclooctyl radical, and isooctyl radicals such as the 2,2,4-trimethylpentyl radical, nonyl radicals such as the n-nonyl radical, decyl radicals such as the n-decyl radical and the adamantyl radical, cycloalkyl radicals such as cyclopropyl, cyclopentyl, cyclohexyl, cycloheptyl and methylcyclohexyl radicals, unsaturated radicals such as the allyl, 5-hexenyl, 7-octenyl, cyclohexenyl and styryl radicals, aryl radicals such as phenyl radicals, o-, m- or p-tolyl radicals, xylyl radicals and ethylphenyl radicals, aralkyl radicals such as the benzyl radical and the α- and β-phenylethyl radicals.

Further examples of $R^7$ are substituted radicals such as acetoxy, hydroxyaryl, methoxyaryl, ethoxyaryl, isopropoxyaryl, butoxyaryl and phenoxyaryl radicals such as 2-methoxyphenyl, 3-methoxyphenyl, 4-methoxyphenyl, 2,4-dimethoxyphenyl, acetoxyphenyl and methoxyhydroxyphenyl radical. Examples of halogenated $R^7$ radicals are haloalkyl radicals such as the trifluoromethyl radical, 3,3,3-trifluoro-n-propyl radical, the 2,2,2,2',2',2'-hexafluoroisopropyl radical, the heptafluoroisopropyl radical and haloaryl radicals such as the o-, m-, p-chlorophenyl radical, o-, m-, p-bromophenyl radical, o-, m- or p-fluorophenyl radical, 3,4-dichlorophenyl, 2,4-dichlorophenyl, 3,5-dichlorophenyl, 3,4-dibromophenyl, 2,4-dibromophenyl and pentafluorophenyl radical.

The $R^7$ radical is preferably a hydrocarbon radical having from 1 to 10 carbon atoms, particular preference being given to the tert-butyl radical, the acetoxy radical, and the phenyl radical.

The platinum catalysts (D) are preferably platinum complexes of the formula (I), (V), (VII), (VIII) and (IX), where $R^1$ is COD or nbd, where "COD" represents 1,5-cyclooctadiene and "nbd" represents bicyclo[2.2.1]hepta-2,5-diene.

Among the platinum catalysts (D), particular preference is given to CODPt(—N(Ph)-C(=O)-(Ph)N—), CODPt(—N(—C(=O)CH$_3$)—C(=O)—(CH$_3$(O=)C—)N—), (—N(—C(=O)(CH$_2$)$_{16}$CH$_3$)—C(=O)—(CH$_3$(CH$_2$)$_{16}$(O=)C—)N—), CODPt(—N(—C(=O)CH$_3$)—C(=O)-(Ph)N—), CODPt(—N(—C(=O)(CH$_2$)$_{16}$CH$_3$)—C(=O)-(Ph)N—), CODPt(—N(—C(=O)CH$_3$)—C(=O)—((CH$_3$)$_3$C—)N—), COD(Pt(—N(C$_6$H$_4$—CH$_3$)—C(=O)—(CH$_3$—C$_6$H$_4$)N—), CODPt(—N(Ph)-C(=O)—(C$_6$H$_{13}$)N—), COD(Pt(—N(C$_6$H$_4$—CH$_3$)—C(=O)—(C$_6$H$_{13}$)N—), nbdPt(—N(Ph)-C(=O)-(Ph)N—), nbdPt(—N(Ph)-C(=O)—(C$_6$H$_{13}$)N—), nbdPt(—N(—C(=O)CH$_3$)—C(=O)—(CH$_3$(O=)C—)N—), nbdPt(—N(—C(=O)CH$_3$)—C(=O)-(Ph)N—) and compounds (D) of the formula (VII), (VIII) and (IX).

Examples of the platinum catalysts (D) of the average general formulae (VII), (VIII) and (IX) are platinum complexes of the formula (VII), (VIII) and (IX) where $R^1$ is COD or nbd. COD represents 1,5-cyclooctadiene and nbd represents bicyclo[2.2.1]hepta-2,5-diene. Further examples are CODPt-(Ph)N—C(=O)—N—(CH$_2$)$_3$—Si(Me)-((O—Si(Me)$_3$)$_2$, CODPt-(Ph)N—C(=O)—N—(CH$_2$)$_3$—Si(Me)$_3$, CODPt-(Ph)N—C(=O)—N—(CH$_2$)$_3$—Si(Me)$_2$-(CH$_2$)$_7$—CH$_3$, CODPt-(Ph)N—C(=O)—N—(CH$_2$)$_3$—Si(Me)$_2$-(CH$_2$)$_{17}$—CH$_3$, CODPt-(Ph)N—C(=O)—N—(CH$_2$)$_3$—Si(Me)$_3$, nbdPt-(Ph)N—C(=O)—N—(CH$_2$)$_3$—Si(Me)$_2$-(CH$_2$)$_7$—CH$_3$, CODPt-((CH$_3$)$_3$C—)N—C(=O)—N—(CH$_2$)$_3$—Si(Me)-((O—Si(Me)$_3$)$_2$, CODPt—(C$_{18}$H$_{37}$)N—C(=O)—N—(CH$_2$)$_3$—Si(Me)$_3$, CODPt-(Ph)N—C(=O)—N—(CH$_2$)$_3$—Si(Me)$_2$-(O—Si(Me)$_2$)$_g$—O—Si(Me)$_2$-(CH$_2$)$_3$—N—C(=O)—N(Ph)-PtCOD, CODPt—(Cl-Ph)N—C(=O)—N—(CH$_2$)$_3$—Si(Me)$_2$-(O—Si(Me)$_2$)$_g$—O—Si(Me)$_2$-(CH$_2$)$_3$—N—C(=O)—N(Ph-Cl)—PtCOD, CODPt—(C$_{18}$H$_{37}$)N—C(=O)—N—(CH$_2$)$_3$—Si(Me)$_2$-(O—Si(Me)$_2$)$_g$-O—Si(Me)$_2$-(CH$_2$)$_3$—N—C(=O)—N(C$_{18}$H$_{37}$)—PtCOD, CODPt-(Ph)N—C(=O)—N—(CH$_2$)$_2$—N(—C(=O)—NH-Ph)-(CH$_2$)$_3$—Si(Me)$_2$-(O—Si(Me)$_2$)$_g$-O—Si(Me)$_2$-(CH$_2$)$_3$—N(—C(=O)—NH-Ph)-CH$_2$)$_2$—N—C(=O)—NPh-PtCOD, CH$_3$O—C$_6$H$_3$—N—(PtCOD)—C(=O)—N—C$_6$H$_3$(—CH$_3$)—N(H)—C(=O)—N(H)—(CH$_2$)$_3$—(Si(CH$_3$)$_2$—O)$_{21}$—Si(CH$_3$)$_2$—(CH$_2$)$_3$—N(H)—C(=O)—N(H)—C$_6$H$_3$(—CH$_3$)—N—C(=O)—N—(PtCOD)—C$_6$H$_3$—OCH$_3$ where g is equal to 0 or an integer from 1 to 500, preference being given to from 1 to 100 and particular preference to from 1 to 50, and Me is a methyl group.

Particular preference is given to platinum complexes of the formula (VII) and (VIII) where $R^1$ is COD or nbd.

The present invention further provides a process for preparing crosslinkable polyorganosiloxane compositions comprising (A) polyorganosiloxanes which have radicals having aliphatic carbon-carbon multiple bonds, (B) polyorganosiloxanes with Si-bonded hydrogen atoms, or, instead of (A) and (B) or in addition thereto, (C) polyorganosiloxanes which have SiC-bonded radicals with aliphatic carbon-carbon multiple bonds and Si-bonded hydrogen atoms, and (D) platinum catalysts selected from the group consisting of

(I)

(II)

(III)

(IV)

(V)

(VI)

and also silanes and siloxanes comprising at least one of the units of the average general formulae (VII), (VIII) or (IX)

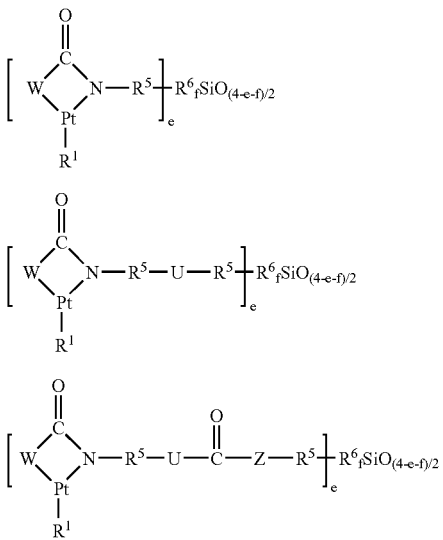

(VII)

(VIII)

(IX)

in which
R¹ is an optionally substituted diene which is bonded to platinum by at least one bond and is an unbranched or branched chain having from 4 to 18 carbon atoms, a cyclic or bicyclic system having from 6 to 28 carbon atoms,
e is 0, 1, 2 or 3,
f is 0, 1, 2 or 3, with the proviso that e+f is 4 for silanes and is 0, 1, 2 or 3 for siloxanes, and that at least one unit where e does not equal 0 is present,
U is O, $NR^2$, or $N-C(=O)-NR^2$
W is $NR^7$, $C(R^3)-CO_2R^3$, $C(R^3)-C(=Z)-R^3$, S, O, or $C(R^3)_2$
X is $NR^2$, $C(R^3)-CO_2R^3$, $C(R^3)-C(=Z)-R^3$, S, O, or $C(R^3)_2$
Y is $NR^2$, $C(R^3)-CO_2R^3$, $C(R^3)-C(=Z)-R^3$, S, O, or $C(R^3)-CN$
Z is O, S, Se, $NR^2$, or $CR^4{}_2$
$R^2$ are each independently hydrogen or a monovalent optionally substituted hydrocarbon radical having from 1 to 24 carbon atoms which optionally contains one or more heteroatoms in the chains or the rings, preferably a heteroatom selected from among the O, S, Se, N, P, and As,
$R^3$ are each independently hydrogen, or a monovalent, optionally substituted hydrocarbon radical having from 1 to 28 carbon atoms,
$R^4$ are each independently hydrogen, or a monovalent, optionally substituted hydrocarbon radical having from 1 to 24 carbon atoms, with the proviso that at least one radical is —CN, —$CO_2R^3$, —C(=O)—$R^3$, —$NO_2$, —C(=O)—H or halogen,
$R^5$ are each independently divalent, optionally substituted hydrocarbon radicals having from 1 to 26 carbon atoms,
$R^6$ are each independently monovalent, optionally substituted hydrocarbon radicals having from 1 to 20 carbon atoms and
$R^7$ are each independently monovalent, optionally substituted hydrocarbon radicals having from 1 to 20 carbon atoms.
which comprises mixing at least constituents (A), (B), (C) and (D).

Preference is given to a one-component version of the compositions. To this end, at least constituents (A), (B) and (D) are mixed in one component. In a further preferred embodiment, constituents (C) and (D) are mixed in one component. Even though preference is given to a one-component version of the inventive crosslinkable polyorganosiloxane compositions, they may also be used as two-component or multicomponent compositions. For example, constituents (A) and (D) are used in a first component, and (B) and optionally (A) in the second component.

The present invention also provides silicone elastomers which are obtained by crosslinking the inventive crosslinkable polyorganosiloxane compositions. The inventive crosslinkable compositions have the advantage that they can be prepared in a simple process using easily obtainable starting materials and thus in a more economically viable manner. The compositions have the additional advantage that they have good storage stability as a one-component formulation at 25° C. and ambient pressure, and crosslink very rapidly only at elevated temperature. Despite having good storage stability in the course of room temperature storage, the compositions also exhibit corresponding to long pot life, and low onset temperatures. In addition, despite good storage stability, they have high crosslinking rates at elevated temperatures.

The inventive silicone compositions have the advantage that in two-component formulations, after mixing of the two components, crosslinkable silicone compositions whose processability is retained over a prolonged period at 25° C. and ambient pressure, corresponding to very long pot lives, and which crosslinks very rapidly only at elevated temperature, are produced.

In the preparation of the inventive crosslinkable compositions, it is of great advantage that the platinum catalyst (D) can be incorporated easily; that the crosslinked silicone rubbers have excellent transparency; that the crosslinked silicone rubbers do not have any yellowing, as is often observed when other platinum catalysts are used; that the platinum catalysts (D) do not form any platinum colloids at the end of the crosslinking reaction; and that the hydrosilylation reaction does not slow with reaction time.

The inventive platinum complexes are useful as catalysts for the well-known hydrosilylation reaction in organosilicon chemistry, as a catalyst for the hydrogenation of unsaturated organic compounds or polymers, and for the oligomerization of acetylene and other alkynes.

The inventive platinum catalysts have the further advantage that terminal double bonds are not shifted inward in the hydrosilylation, as a result of which a low-reactivity isomerized starting material would remain. The inventive platinum catalysts have the further advantage that no platinum colloids are formed and their use does not result in any discoloration.

The present invention also provides a process for preparing silicone elastomers, which comprises crosslinking the inventive crosslinkable polyorganosiloxane compositions, preferably under the influence of heat or radiation, for example UV or microwave radiation. Particular preference is given to crosslinking the inventive crosslinkable polyorganosiloxane compositions at temperatures of from 25 to 200° C., in particular from 50 to 150° C.

The silicone elastomers obtained in accordance with the invention can be used for all purposes for which organopolysiloxane compositions crosslinkable to elastomers or elastomers are useful. The silicone elastomers obtained in accordance with the invention are particularly suitable for use as embedding compositions for electric or electronic devices, as impression materials, coating materials and for the production of moldings, for example in the injection-molding process, vacuum-extrusion process, extrusion process, casting and compression molding.

The preparation of the platinum compounds may take place, for example, for some embodiments, as described in J. ORGANOMET. CHEM. 526 (1996) 303-312, J. ORGANOMET. CHEM. 556 (1998)75-88, J. CHEM. SOC. DALTON TRANS. (1992) 409, J. CHEM. SOC. DALTON TRANS. (1994) 3085 and CHEM. COMMUN. (1996) 211.

The present invention further provides a process for preparing the inventive platinum catalysts (D) of the general formulae (VII), (VIII) and (IX), which comprises a) initially charging $CODPtCl_2$, the appropriate ligand and silver oxide in a solvent, b) reacting the reaction mixture while supplying heat and c) removing the silver compound after the reaction mixture has been cooled in which $CODPtCl_2$ is dichloro(cycloocta-1,5-diene)platinum(II).

In a preferred embodiment, the solution is finally concentrated to dryness and the product is optionally recrystallized. All reactions are preferably carried out under protective gas atmosphere, for example nitrogen, helium or argon. Preferred solvents are all aprotic solvents, in particular dichloromethane, acetone and tetrahydrofuran (THF), particularly chlorinated solvents and in particular dichloromethane or chloroform. Preference is given to effecting the reaction with heating under reflux. Alternatively, the base used instead of silver oxide may be sodium hydroxide or potassium hydroxide in a solvent mixture of dichloromethane and THF.

EXAMPLES

In the examples which follow, which demonstrate the performability of the invention in principle but without having restrictive character, the base used in the reactions was predominantly silver oxide ($Ag_2O$), although other bases are also possible. Either commercially available silver oxide (for example from ALDRICH GmbH) or freshly prepared silver oxide was used; the latter was prepared by reacting silver nitrate with sodium hydroxide under protective gas atmosphere. To this end, 4.40 parts of silver nitrate were dissolved in 40 parts of water, and a solution of 1.10 parts of sodium hydroxide dissolved in 40 parts of water was added dropwise. After stirring for 2 hours and leaving to stand overnight, the $Ag_2O$ precipitate formed was filtered off by means of a glass frit, and washed with 100 ml of water, 100 ml of methanol and 50 ml of dichloromethane. Subsequently, the silver oxide was dried to constant weight under reduced pressure.

All solvents were used without further drying as purchased. All parts are parts by weight. $CODPtCl_2$ and $nbdPtCl_2$ represent dichloro(cycloocta-1,5-diene)platinum(II) and dichloro(2,5-norbornadiene)platinum(II) respectively.

General Preparation Method for Platinum Complexes:

All reactions were carried out under protective gas atmosphere, preferably nitrogen or argon. $CODPtCl_2$, ligand, silver oxide and from 50 to 200 parts of dichloromethane were heated under reflux for from 4 to 18 hours. Finally, the mixture was cooled to room temperature and filtered in order to remove the silver compounds. The solution was concentrated to dryness and the product was recrystallized from dichloromethane-diethyl ether or dichloromethane-heptane.

Catalyst 1:

0.5 part of $CODPtCl_2$, 0.29 part of N,N-diphenylurea, 2.1 parts of silver oxide and 50 parts of dichloromethane were heated under reflux for 7 hours. After the above-described general workup, 0.42 part of a platinum complex of the formula

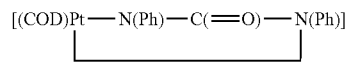

was obtained.

Catalyst 2:

The preparation is effected analogously to the preparation of catalyst 1, with the exceptions that, instead of $CODPtCl_2$, $nbdPtCl_2$ was used, and the target product was obtained by extraction by means of Soxhlet apparatus. 0.2 part of the target product was obtained, which has the structure

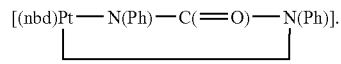

Catalyst 3:

1.0 part of $CODPtCl_2$, 0.60 part of N-(n-hexyl)-N-phenylurea, 2.9 parts of silver oxide freshly prepared by the aforementioned process and 200 parts of dichloromethane were heated under reflux for 6 hours. After the above-described workup, 1.3 parts of a platinum complex of the formula

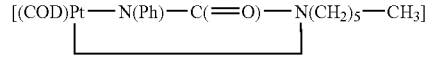

were obtained.

Catalyst 4:

1.5 parts of $CODPtCl_2$, 0.61 part of N,N-diacetylurea, 2.9 parts of silver oxide freshly prepared by the aforementioned process and 200 parts of dichloromethane were heated under reflux for 7 hours. After the above-described workup, 0.95 part of a platinum complex of the formula

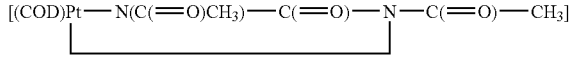

was obtained.

Catalyst 5:

1.0 part of $CODPtCl_2$, 0.45 part of phenylphosphonic acid, 2.9 parts of commercially available silver oxide and 50 parts of dichloromethane were heated under reflux for 7.5 hours. After the workup, 0.9 part of a platinum complex of the formula

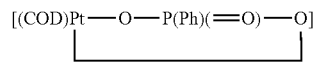

was obtained.

Catalyst 6:

1.5 parts of $CODPtCl_2$, 0.75 part of N-acetyl-N'-phenylurea, 2.9 parts of silver oxide freshly prepared by the aforementioned process and 200 parts of dichloromethane were heated under reflux for 7 hours. After the workup, 1.0 part of a platinum complex of the formula

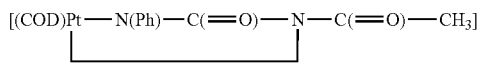

was obtained.

Catalyst 7:

0.5 part of $CODPtCl_2$, 0.16 part of N-acetylglycine, 2.9 parts of silver oxide freshly prepared by the aforementioned process and 50 parts of dichloromethane were heated under reflux for 7 hours. After the workup, 0.46 part of a platinum complex of the formula

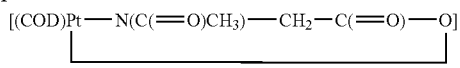

was obtained.

Catalyst 8:

0.102 part of $CODPtCl_2$, 0.042 part of D,L-mandelic acid, 0.807 part of silver oxide and 200 parts of dichloromethane were heated under reflux for 5 hours. After the workup, 0.100 part of a platinum complex of the formula

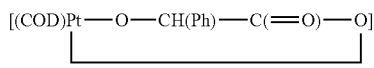

was obtained.

Catalyst 9:

2.65 parts of phenyl isocyanate are dissolved in 10 parts of diethyl ether and added dropwise at room temperature to a solution of 21.15 parts of a poly(dimethyl)siloxane with aminopropyldimethylsiloxy end groups and 20 dimethylsiloxy groups in the chain (the preparation of these compounds is known to those skilled in the art) and 50 parts of diethyl ether. After 2 hours, the solvent is removed under reduced pressure and 20.7 parts of an oil (ligand 1) with the following formula are obtained: Ph-N(H)—C(=O)—N(H)—$(CH_2)_3$—$(Si(CH_3)_2$—$O)_{21}$—$Si(CH_3)_2$—$(CH_2)_3$—N(H)—C(=O)—N(H)-Ph.

One part of $CODPtCl_2$, 3.16 parts of ligand 1, 2.9 parts of freshly prepared silver oxide and 200 parts of dichloromethane were heated under reflux for 3 hours. After the workup, 3.9 parts of a resinous product with the formula

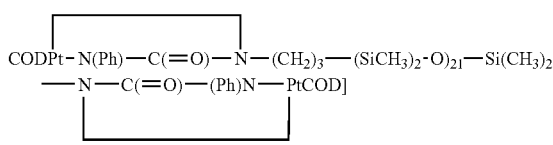

were obtained.

Catalyst 10:

5.24 parts of phenyl isocyanate are dissolved in 20 parts of diethyl ether and added dropwise at room temperature to a solution of 54.4 parts of a poly(dimethyl)siloxane with aminoethylaminopropyldimethylsiloxy end groups and 47 dimethylsiloxy groups in the chain (the preparation of these compounds is known to those skilled in the art) and 50 parts of diethyl ether. After 1 hour, the solvent is removed under reduced pressure and 59.3 parts of an oil (ligand 2) with the following formula are obtained: Ph-N(H)—C(=O)—N(H)—$(CH_2)_2$—N[—C(=O)—N(H)Ph]-$(CH_2)_3$—$(Si(CH_3)_2 O)_{48}$—$Si(CH_3)_2$—$(CH_2)_3$—N[—C(=O)N(H)Ph]-$(CH_2)_2$N(H)—C(=O)—N(H)-Ph.

One part of $CODPtCl_2$, 7.94 parts of ligand 2, 2.9 parts of freshly prepared silver oxide and 200 parts of dichloromethane were heated under reflux for 6 hours. After the workup, 8.3 parts of a highly viscous product with the formula

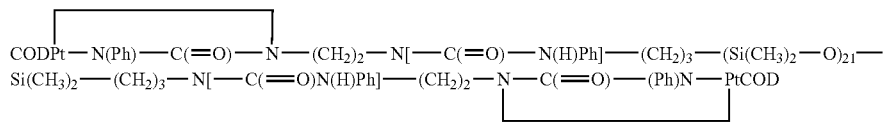

were obtained.

Catalyst 11:

6.15 parts of m-anisidine are dissolved in 50 parts of diethyl ether and added dropwise at room temperature to a solution of 10 parts of toluylene 2,4-diisocyanate dissolved in 130 ml of diethyl ether. During the reaction, a white precipitate forms and is filtered off with a frit, washed with heptane and dried under reduced pressure (ligand 3).

6.23 parts of ligand 3 are dissolved in 80 ml of dried THF and admixed with a solution of 21.15 parts of a poly(dimethyl)siloxane with aminopropyldimethylsiloxy end groups and 20 dimethylsiloxy groups in the chain (the preparation of these compounds is known to those skilled in the art) and 30 parts of THF. After 3 hours, the solvent is removed under reduced pressure and 25.5 parts of an oil (ligand 4) with the formula $CH_3O$—$C_6H_3$—N(H)—C(=O)—N(H)—$C_6H_3$(—$CH_3$)—N(H)—C(=O)—N(H)—$(CH_2)_3$—$(Si(CH_3)2$-$O)_{21}$—$Si(CH_3)_2$—$(CH_2)_3$—N(H)—C(=O)—N(H)—$C_6H_3$(—$CH_3$)—N(H)—C(=O)—N(H)—$C_6H_3$—$OCH_3$ are obtained.

One part of $CODPtCl_2$ 3.66 parts of ligand 4, 3.2 parts of silver oxide and 200 parts of acetone were heated under reflux for 6 hours. After the workup, 4.4 parts of a resinous product with the formula

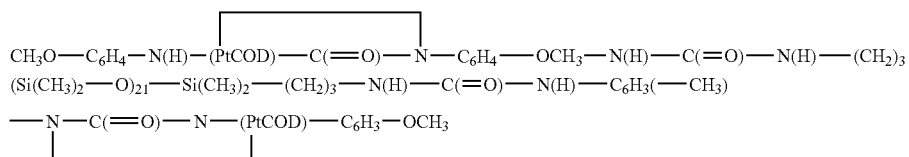

were obtained.

Example 1

50.0 parts of a vinyldimethylsiloxy-terminated polydimethylsiloxane with a viscosity of 20 Pa·s, 0.033 part of 1-ethynyl-1-cyclohexanol and 1 part of SiH crosslinker were mixed homogeneously with the aid of an RE 162 stirrer from Janke & Kunkel IKA-Labortechnik, the SiH crosslinker being a copolymer of dimethylsiloxy and methylhydrosiloxy and trimethylsiloxy units with a viscosity of 330 mPa—s and a content of Si-bonded hydrogen of 0.46% by weight. Subsequently, 0.0014 part of catalyst 1, corresponding to a content of 10 ppm of Pt based on the overall composition, dissolved in 0.5 ml of methylene chloride was stirred in at room temperature.

Examples 2 to 11 correspond to Example 1 except that different catalysts were used. The mixtures can be taken from Tables 1a and 1b. The amount of the catalysts used gave rise in each case to 10 ppm of Pt in the overall composition.

Example 12

The procedure described in Example 1 is repeated with the modification that, before the catalyst addition, 47 mg of 3-methyl-1-dodecyn-3-ol were stirred in instead of the ethynylcyclohexanol.

Comparative Example 1

The procedure described in Example 1 is repeated with the modification that, instead of catalyst 1, 10 ppm of platinum in the form of platinum-divinyltetramethyldisiloxane complex in vinyl-terminated polydimethylsiloxane were used.

Comparative Example 2

The procedure described in Example 1 is repeated with the modification that, instead of catalyst 1, 0.001 part of 1,5-cyclooctadiene platinum dichloride was used.

Example 13

A laboratory kneader was initially charged with 255 parts by weight of a vinyldimethylsiloxy-terminated polydimethylsiloxane having a viscosity of 20 Pa·s which were heated to 150° C. and admixed with 180 parts by weight of a hydrophobic pyrogenic silica with a specific BET surface area of 300 m²/g and a carbon content of 3.95% by weight. This formed a highly viscous mass which was subsequently diluted with 165 parts by weight of the abovementioned polydimethylsiloxane. Kneading under reduced pressure (10 mbar) at 150° C. removed volatile constituents over one hour.

487.29 parts of the thus prepared base composition were mixed on a roller at a temperature of 25° C. with 0.160 part of 1-ethynyl-1-cyclohexanol, 10.55 parts of SiH crosslinker and 2.0 parts of catalyst batch to give a homogeneous composition, the SiH crosslinker being a copolymer of dimethylsiloxy and methylhydrosiloxy and trimethylsiloxy units having a viscosity of 330 mPa·s and a content of Si-bonded hydrogen of 0.46% by weight, and the catalyst batch being a mixture of abovementioned vinylpolydimethylsiloxane and catalyst 1, whose preparation is described above (platinum content 5 ppm based on the overall composition).

Example 14

589.4 parts of a vinyldimethylsiloxy-terminated polydimethylsiloxane having an average of three vinyl groups in the chain and a Brabender plasticity of 630 mkp, corresponding to a mean molar mass of approx. 500,000 g/mol, were mixed with 252.6 parts of a hydrophobic pyrogenic silica with a BET surface area of 300 m²/g and a carbon content of 3.95% by weight, which was metered in in portions, for 4 hours in a kneader to give a homogeneous composition.

100 parts of the thus obtained base composition were mixed on a roller at a temperature of 20° C. with 0.05 part of 1-ethynylcyclohexan-1-ol, 1.2 parts of SiH crosslinker and 0.00066 part of catalyst 1, dissolved in 1 ml of dichloromethane, to give a homogeneous composition, the SiH crosslinker being a copolymer of dimethylsiloxy and methylhydrosiloxy and trimethylsiloxy units having a viscosity of 310 mPa·s at 25° C. and a content of Si-bonded hydrogen of 0.46% by weight.

Example 15

The procedure described in Example 14 is repeated with the modification that the catalyst used was 0.0013 part of platinum complex 6 dissolved in 1 part of dichloromethane.

Example 16

The procedure described in Example 14 is repeated with the modification that the catalyst used was 0.0011 part of platinum complex 7 dissolved in 1 part of dichloromethane.

The thermal curing properties of the polyorganosiloxane compositions prepared in Examples 1 to 12 and Comparative Examples 1 and 2 were measured with a Dynamic Analyzer RDA II from Rheometrics with a heating curve from 30 to 200° C. and with a heating rate of 5° C./minute. The temperature which corresponds to the 4% value of the maximum torque was defined as the onset temperature $a_T$. For the quantitative determination of the storage stability, the prepared formulations were stored at room temperature (RT), and the time taken for the initial viscosity value to double, in each case measured in days, was determined. The results are shown in Tables 1a and 1b.

TABLE 1a

| | Example | | | | | | |
|---|---|---|---|---|---|---|---|
| | 1 | 2 | 3 | 4 | 5 | 6 | 7 |
| Catalyst | 1 | 2 | 3 | 4 | 5 | 6 | 7 |
| $a_T$ [° C.] | 126 | 127 | 105 | 117 | 103 | 108 | 106 |

TABLE 1a-continued

| | Example | | | | | | |
|---|---|---|---|---|---|---|---|
| | 1 | 2 | 3 | 4 | 5 | 6 | 7 |
| Storage at RT [days] | >300 | >100 | >30 | >40 | >20 | >40 | >40 |

TABLE 1b

| | Example | | | | | | |
|---|---|---|---|---|---|---|---|
| | 8 | 9 | 10 | 11 | 12 | C1 | C2 |
| Catalyst | 8 | 9 | 10 | 11 | 3 | | |
| $a_T$ [° C.] | 105 | 104 | 105 | 118 | 108 | 100 | 98 |
| Storage at RT [days] | >30 | >50 | >50 | >70 | >50 | 10 | 3 |

The thermal curing properties of the polyorganosiloxane compositions prepared in Examples 13 to 16 were measured with a Goettfert Elastograph. The onset temperature a was measured at a heating rate of 10° C./min. The temperature which corresponds to the 4% value of the maximum torque was defined as the onset temperature $a_T$.

The $t_{90}$ value was determined to DIN 53529 T3. The time from the commencement of curing to 90% (=$t_{90}$ value) of the maximum torque was determined at 150° C. The results are listed in Table 2.

For the quantitative determination of the storage stability, the formulations prepared were stored at room temperature (RT) and 40° C., and the time taken for the starting value of the viscosity to double, in each case measured in days, was determined. The results are shown in Table 2.

TABLE 2

| | Examples | | | |
|---|---|---|---|---|
| | 13 | 14 | 15 | 16 |
| $a_T$ [° C.] | 122 | 126 | 123 | 121 |
| $t_{90}$ [s] | 43 | 49 | 41 | 34 |
| Storage at Rt [days] | >80 | >80 | >80 | >80 |
| Storage at 40° C. [days] | >10 | >10 | >10 | >10 |

What is claimed is:

1. A crosslinkable polyorganosiloxane composition comprising
   (A) polyorganosiloxane(s) which bear radicals having aliphatic carbon-carbon multiple bonds,
   (B) polyorganosiloxanes with Si-bonded hydrogen atoms, or,
   (C) instead of or in addition to (A) and (B), polyorganosiloxanes which bear SiC-bonded radicals with aliphatic carbon-carbon multiple bonds and also have Si-bonded hydrogen atoms, and
   (D) at least one platinum catalyst of the structures:

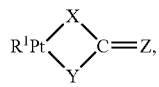
(I)

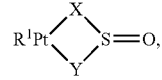
(II)

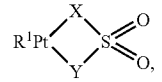
(III)

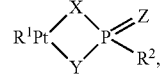
(IV)

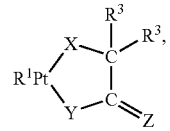
(V)

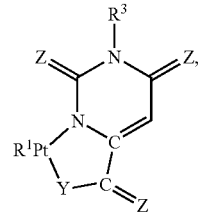
(VI)

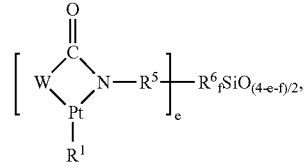
(VII)

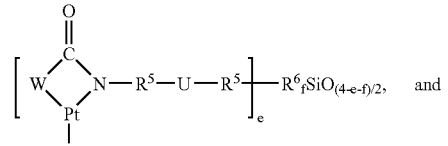
(VIII)

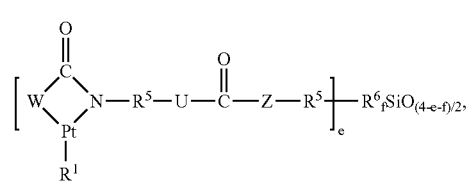
(IX)

in which $R^1$ is an optionally substituted diene which is bonded to platinum by at least one bond and is an unbranched or branched chain having from 4 to 18 carbon atoms, a cyclic or bicyclic system having from 6 to 28 carbon atoms, e is 0, 1, 2 or 3, f is 0, 1, 2 or 3, with the proviso that e+f is 4 for silanes and is 0, 1, 2 or 3 for siloxanes, and that at least one unit where e does not equal 0 is present, U is O, $NR^2$, or N—C(=O)—$NR^2$ W is $NR^7$, $C(R^3)$—$CO_2R^3$, $C(R^3)$—C(=Z)-$R^3$, S, O, or $C(R^3)_2$ X is $NR^2$, $C(R^3)$—$CO_2R^3$, $C(R^3)$—C(=Z)-$R^3$, S, O, or $C(R^3)_2$ Y is $NR^2$, $C(R^3)$—$CO_2R^3$, $C(R^3)$—$C(=Z)$-$R^3$, S, O, or $C(R^3)$—CN Z is O, S, Se, $NR^2$, or $CR^4{}_2$ $R^2$ are each independently hydrogen or a monovalent optionally substituted hydrocarbon radical having from 1 to 24 carbon atoms which optionally contains one or more heteroatoms in the chains or the rings, preferably a heteroatom selected from among the O, S, Se, N, P, and As, $R^3$ are each independently hydrogen, or a monovalent, optionally substituted hydrocarbon radical having from 1 to 28 carbon atoms, $R^4$ are each independently hydrogen, or a monovalent, optionally substituted hydrocarbon radical having from 1 to 24 carbon atoms, with the proviso that at least one radical is —CN, —$CO_2R^3$, —$C(=O)$—$R^3$, —$NO_2$, —$C(=O)$—H or halogen, $R^5$ are each independently divalent, optionally substituted hydrocarbon radicals having from 1 to 26 carbon atoms, $R^6$ are each independently monovalent, optionally substituted hydrocarbon radicals having from 1 to 20 carbon atoms and $R^7$ are each independently monovalent, optionally substituted hydrocarbon radicals having from 1 to 20 carbon atoms.

2. The crosslinkable polyorganosiloxane composition of claim 1, wherein the platinum catalyst is selected from the group consisting of

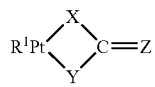
(I)

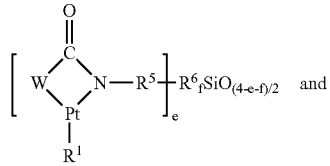
(VII)

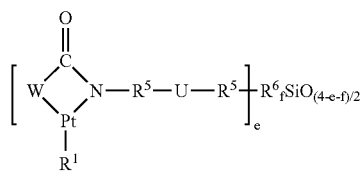
(VIII)

3. The crosslinkable polyorganosiloxane composition of claim 1, wherein $R^1$ is cycloocta-1,5-diene.

4. The crosslinkable polyorganosiloxane composition of claim 1, wherein $R^1$ is bicyclo[2.2.1]hepta-2,5-diene.

5. A process for the preparation of a crosslinkable composition of claim 1, comprising mixing together components (A)-(D) which are employed in the composition.

6. A silicone elastomer prepared by crosslinking the crosslinkable polyorganosiloxane composition of claim 1, said elastomer containing a catalyst (D) or reaction product thereof.

7. A process for preparing a silicone elastomer comprising crosslinking a crosslinkable polyorganosiloxane composition of claim 1 by the influence of at least one of heat or radiation.

8. The composition of claim 1 which is a one component, storage stable composition comprising (A), (B), optionally (C), and (D) in a single component.

9. The composition of claim 1 which is a one component, storage stable composition comprising (C) and (D) in a single component.

10. In an embedding composition for electric or electronic devices, an impression material, a coating material, or molding compound for the production of moldings by injection-molding, vacuum-extrusion molding, extrusion molding, or casting and compression molding, wherein a curable silicone elastomer composition is employed, the improvement comprising selecting as a curable silicone elastomer, the crosslinkable polyorganosiloxane composition of claim 1.

11. A platinum catalyst of the formulae (VII), (VIII) or (IX) useful as a catalyst (D) in the composition of claim 1:

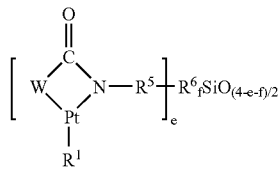
(VII)

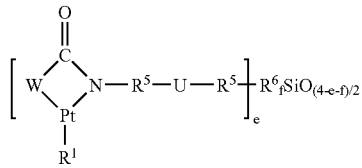
(VIII)

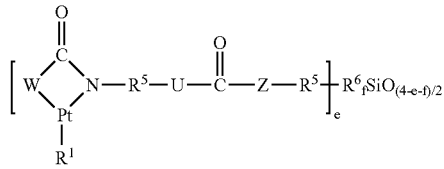
(IX)

in which e is 0, 1, 2 or 3, f is 0, 1, 2 or 3, with the proviso that e+f is 4 for silanes and is 0, 1, 2 or 3 for siloxanes, and that at least one unit where e does not equal 0 is present per molecule, U is O, $NR^2$, or N—$C(=O)$—$NR^2$ W is $NR^7$, $C(R^3)$—$CO_2R^3$, $C(R^3)$—$C(=Z)$-$R^3$, S, O, or $C(R^3)_2$ $R^1$ is an optionally substituted diene which is bonded to platinum by at least one bond and is an unbranched or branched chain having from 4 to 18 carbon atoms, a cyclic or bicyclic system having from 6 to 28 carbon atoms, e is 0, 1, 2 or 3, f is 0, 1, 2 or 3, with the proviso that e+f is 4 for silanes and is 0, 1, 2 or 3 for siloxanes, and that at least one unit where e does not equal 0 is present, U is O, $NR^2$, or N—$C(=O)$—$NR^2$ W is $NR^7$, $C(R^3)$—$CO_2R^3$, $C(R^3)$—$C(=Z)$-$R^3$, S, O, or $C(R^3)_2$ X is $NR^2$, $C(R^3)$—$CO_2R^3$, $C(R^3)$—$C(=Z)$-$R^3$, S, O, or $C(R^3)_2$ Y is $NR^2$, $C(R^3)$—$CO_2R^3$, $C(R^3)$—$C(=Z)$-$R^3$, S, O, or $C(R^3)$—CN Z is O, S, Se, $NR^2$, or $CR^4{}_2$ $R^2$ are each independently hydrogen or a monovalent optionally substituted hydrocarbon radical having from 1 to 24 carbon atoms which optionally contains one or more heteroatoms in the chains or the rings, preferably a heteroatom selected from among the O, S, Se, N, P, and As, $R^3$ are each independently hydrogen, or a monovalent, optionally substituted hydrocarbon radical having from 1 to 28 carbon atoms, $R^4$ are each independently hydrogen, or a monovalent, optionally substituted hydrocarbon radical having from 1 to 24 carbon atoms, with the proviso that at least one radical is —CN, —CO$_2$R$^3$, —C(=O)—R$^3$, —NO$_2$, —C(=O)—H or halogen, $R^5$ are each independently divalent, optionally substituted hydrocarbon radicals having from 1 to 26 carbon atoms, $R^6$ are each independently monovalent, optionally substituted hydrocarbon radicals having from 1 to 20 carbon atoms and $R^7$ are each independently monovalent, optionally substituted hydrocarbon radicals having from 1 to 20 carbon atoms.

12. The platinum catalyst of claim 11, wherein R$^1$ is cycloocta-1,5-diene.

13. The platinum catalyst of claim 11, wherein R$^1$ is bicyclo[2.2.1]hepta-2,5-diene.

14. A process for preparing the platinum catalysts of claim 11, which comprises a) initially charging a platinum compound selected from the group consisting of CODPtCl$_2$, nbdPtCl$_2$, or a mixture thereof, and an organosilicon compound bearing a ligand whose residue is contained in the catalyst, and silver oxide in a solvent, b) reacting the reaction mixture while supplying heat, and c) removing the silver compounds after the reaction mixture has been cooled in which CODPtCl$_2$ is dichloro(cycloocta-1,5-diene)platinum(II), wherein the residue is the portion of the structures VII through IX other than

15. A process for preparing the platinum catalysts as claimed in claim 11, wherein the platinum compound charged in step a) is CODPtCl$_2$.

16. A process for preparing the platinum catalysts as claimed in claim 11, wherein the platinum compound charged in step a) is nbdPtCl$_2$.

* * * * *